United States Patent

Steckel et al.

[11] Patent Number: 5,904,692
[45] Date of Patent: May 18, 1999

[54] NEEDLE ASSEMBLY AND METHOD FOR PASSING SUTURE

[75] Inventors: Mark Steckel, Braintree; Pamela Jacob, Canton, both of Mass.; Robert Morettin, Little Compton, R.I.

[73] Assignee: Mitek Surgical Products, Inc., Westwood, Mass.

[21] Appl. No.: 08/834,639

[22] Filed: Apr. 14, 1997

[51] Int. Cl.⁶ .................................................. A61B 17/04
[52] U.S. Cl. ......................... 606/139; 606/148; 604/272; 128/898
[58] Field of Search .................... 606/139, 148, 606/144, 147; 604/272; 128/898

[56] References Cited

U.S. PATENT DOCUMENTS

| | | | |
|---|---|---|---|
| 2,496,111 | 1/1950 | Turkel . | |
| 2,738,790 | 3/1956 | Todt, Sr. et al. | 606/148 |
| 3,877,434 | 4/1975 | Ferguson et al. . | |
| 3,995,619 | 12/1976 | Glatzer . | |
| 4,172,458 | 10/1979 | Pereyra | 606/148 |
| 4,450,835 | 5/1984 | Asnis et al. | 128/92 EB |
| 4,976,269 | 12/1990 | Mehl | 128/754 |
| 5,026,376 | 6/1991 | Greenberg | 606/96 |
| 5,036,860 | 8/1991 | Leigh et al. | 128/754 |
| 5,059,201 | 10/1991 | Asnis | 606/144 |
| 5,090,419 | 2/1992 | Palestrant | 128/754 |
| 5,149,329 | 9/1992 | Richardson | 604/272 |
| 5,152,749 | 10/1992 | Giesy et al. | 604/272 |
| 5,281,237 | 1/1994 | Gimpelson | 606/144 |
| 5,439,467 | 8/1995 | Benderev et al. | 606/139 |
| 5,544,664 | 8/1996 | Benderev et al. | 128/898 |

FOREIGN PATENT DOCUMENTS

WO9200773  1/1992  WIPO .

*Primary Examiner*—Gary Jackson
*Attorney, Agent, or Firm*—Pandiscio & Pandiscio

[57] ABSTRACT

A needle assembly for passing suture within the body includes a rigid needle having a proximal end and a pointed distal end, and an opening in the distal end extending through the needle for retaining a suture therein; a stop element positioned on the needle proximate to, and spaced from, the proximal end of the needle; a sheath having a lengthwise bore therethrough for slidably retaining the needle; and a lock member engageable with the needle stop element to prevent distal movement of the needle in the sheath bore. The needle distal end is movable to an exposed position for passing the assembly through tissue, and is movable to a shielded position within the sheath for passing the assembly safely past the tissue which is not to be penetrated. There is further contemplated a method for passing suture within the body, using the needle assembly.

29 Claims, 22 Drawing Sheets

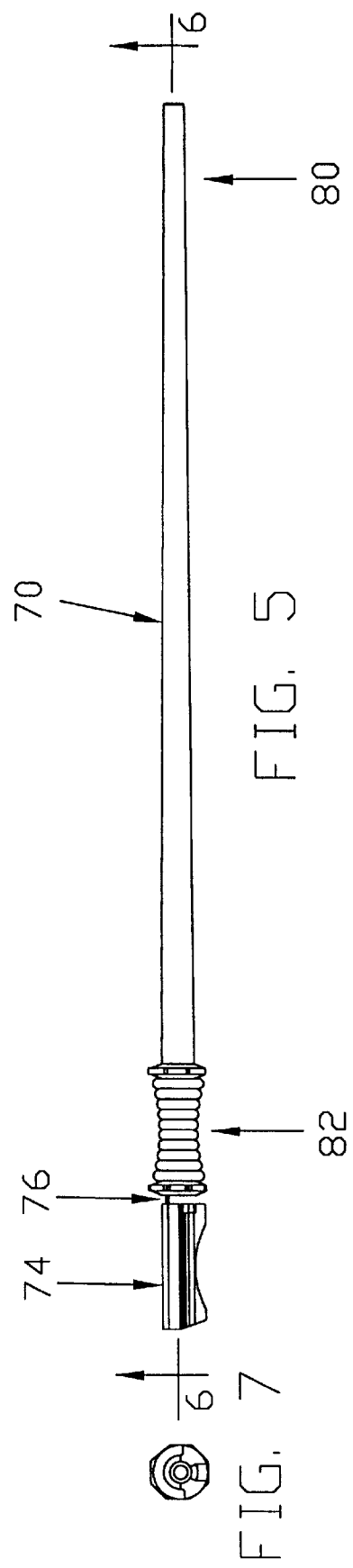
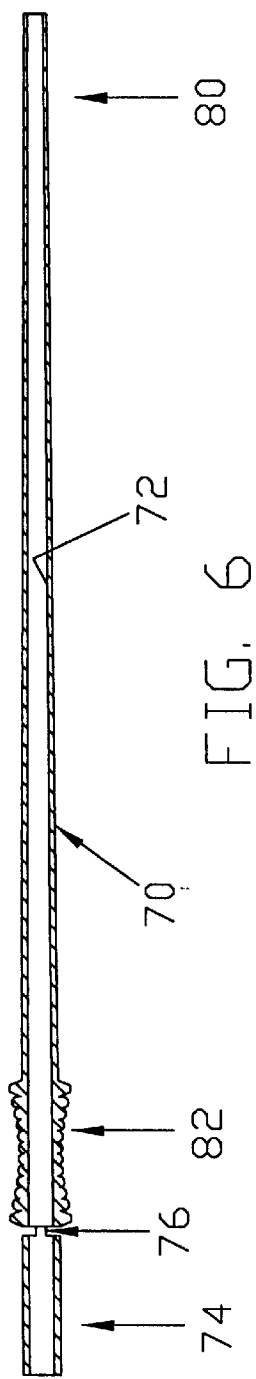

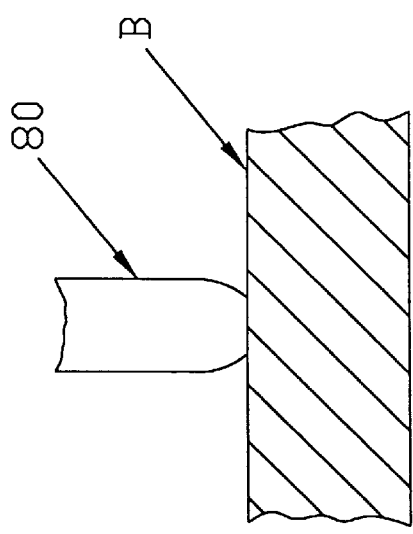
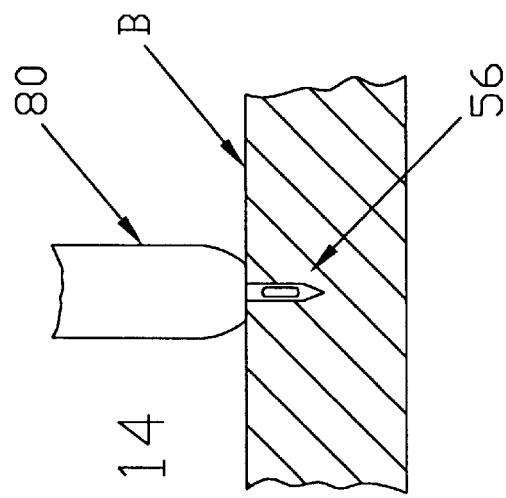
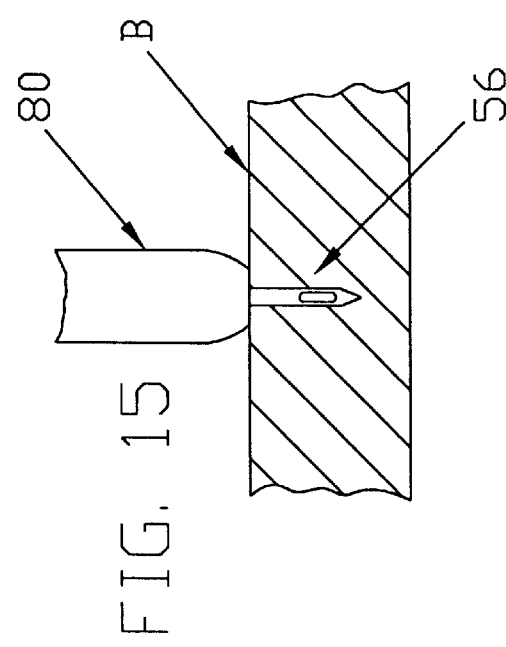

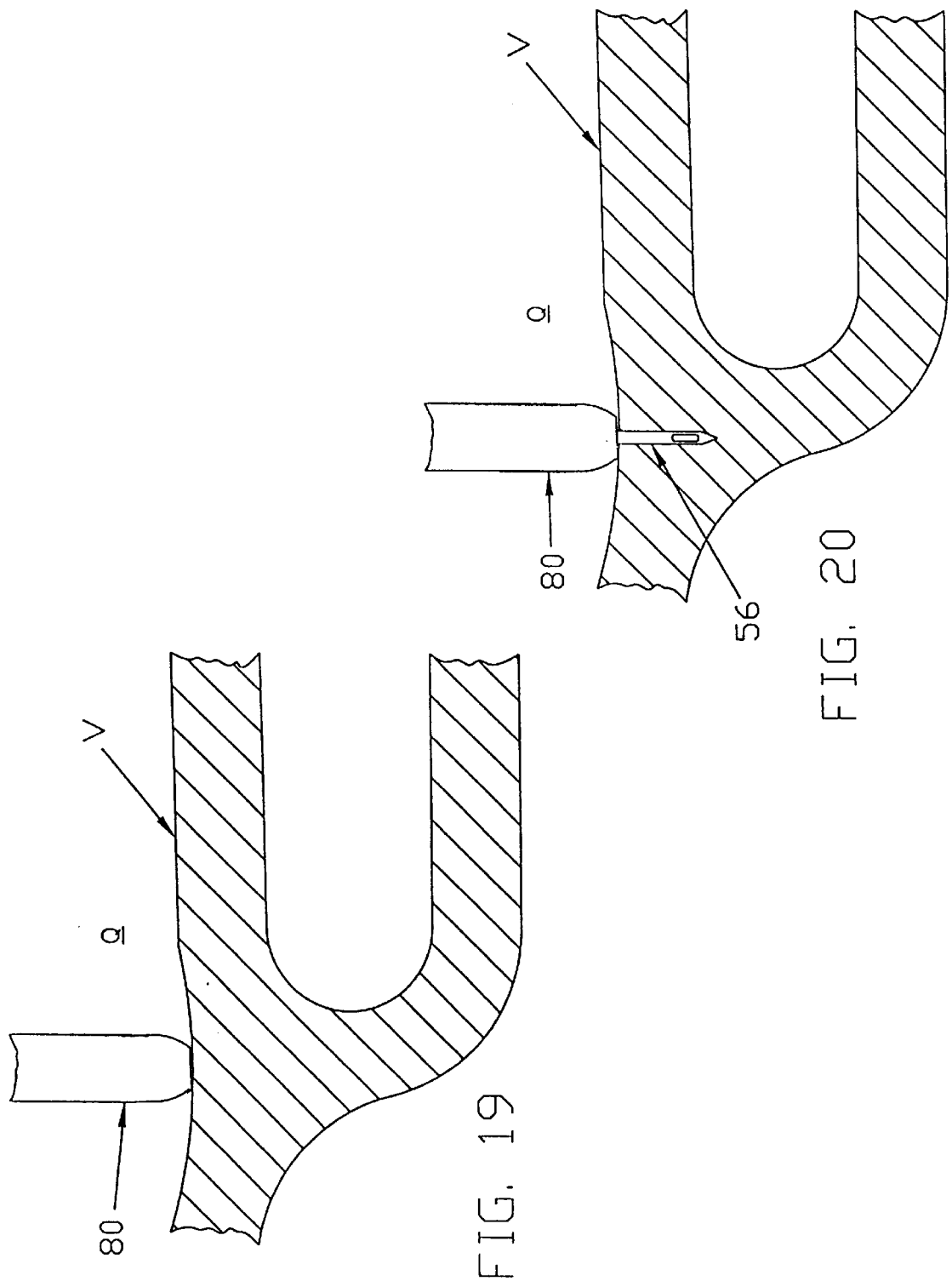

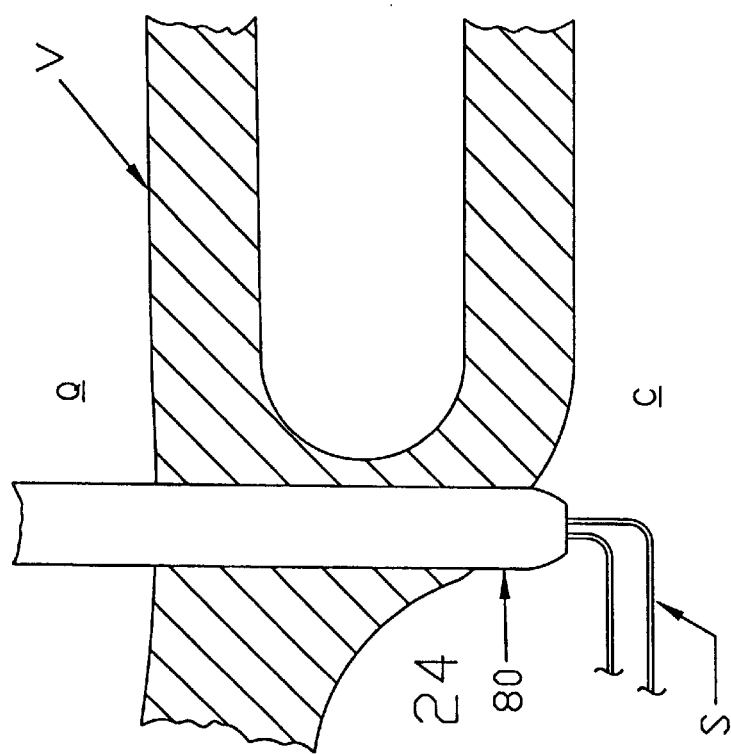
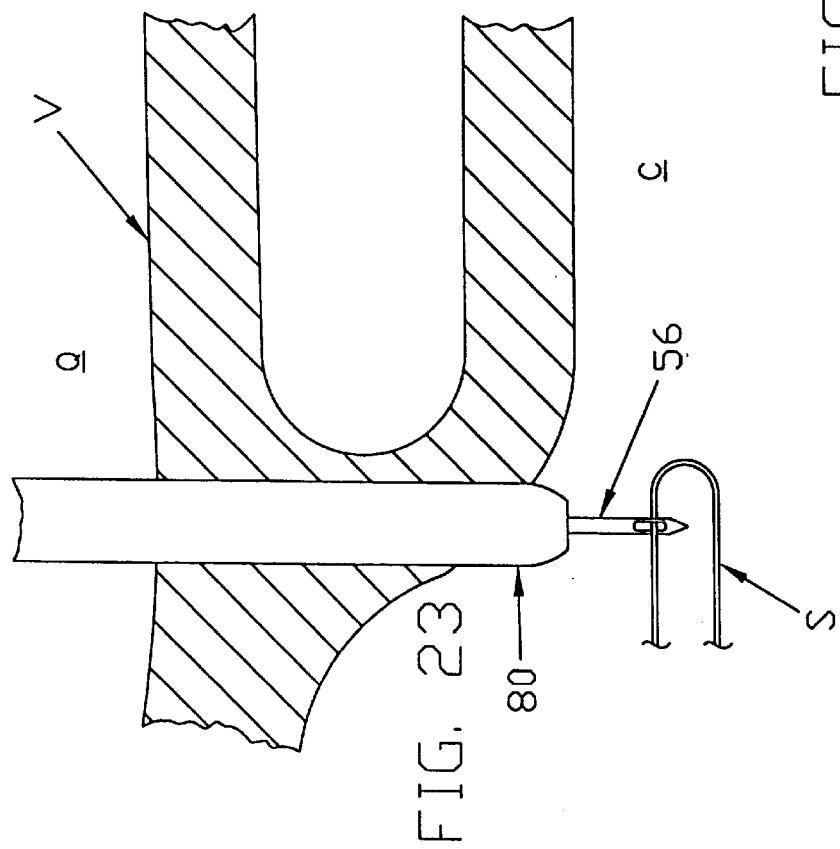

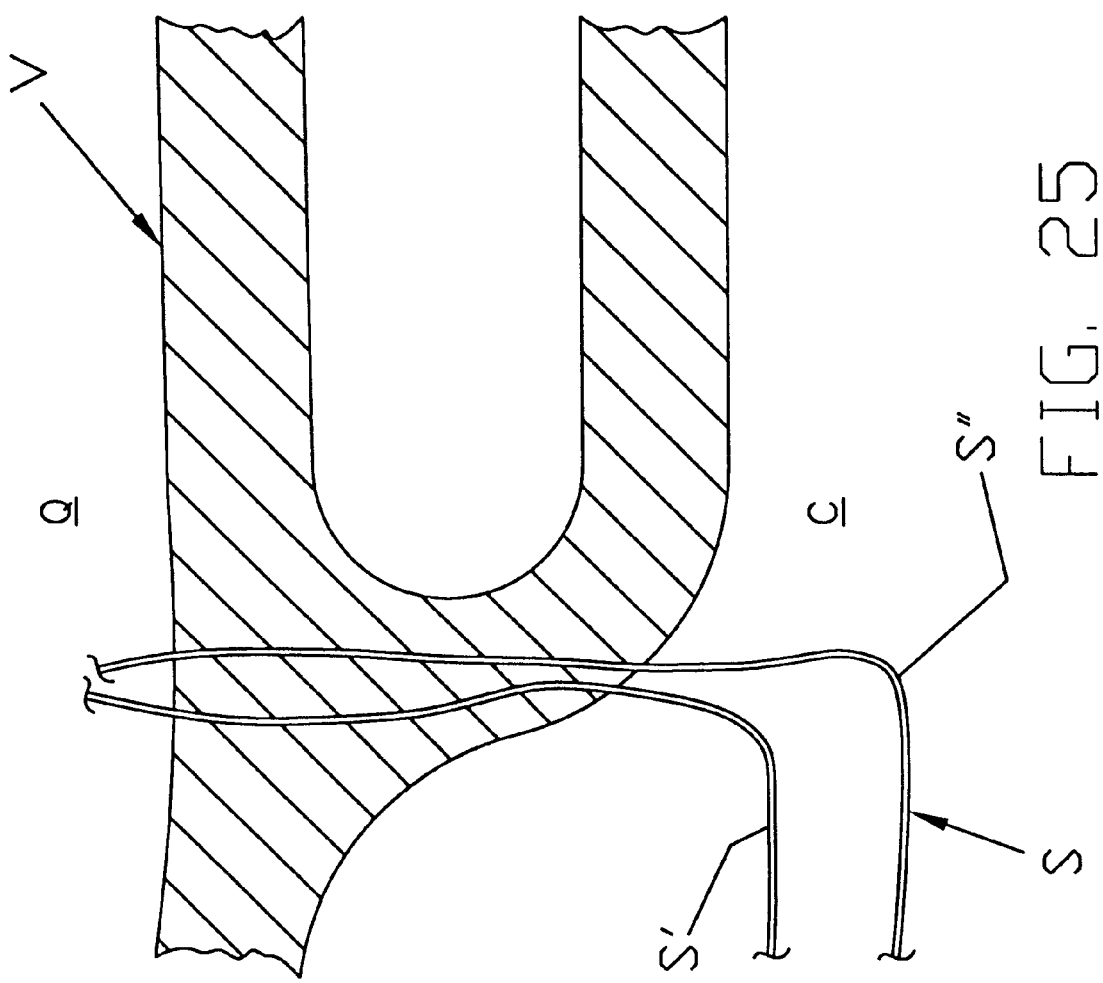

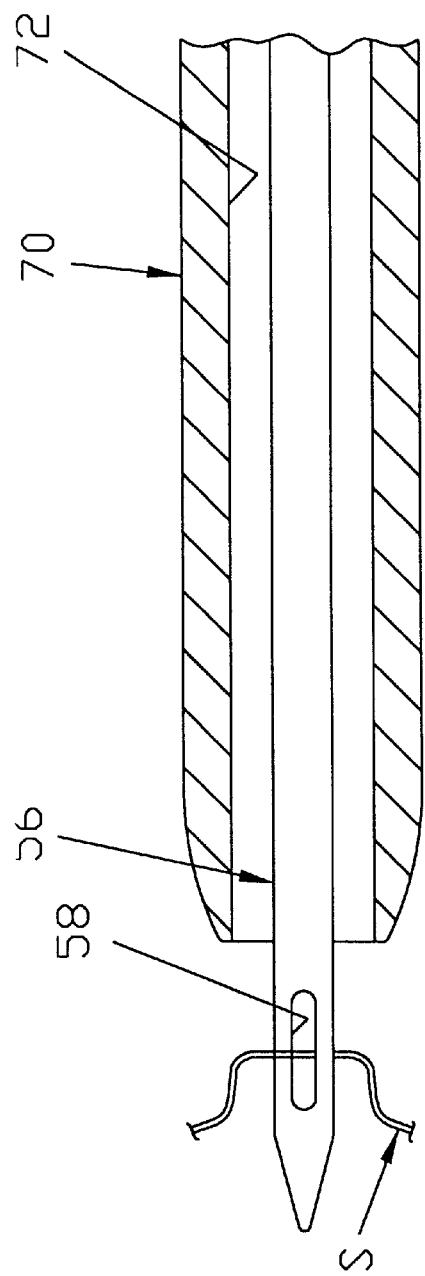
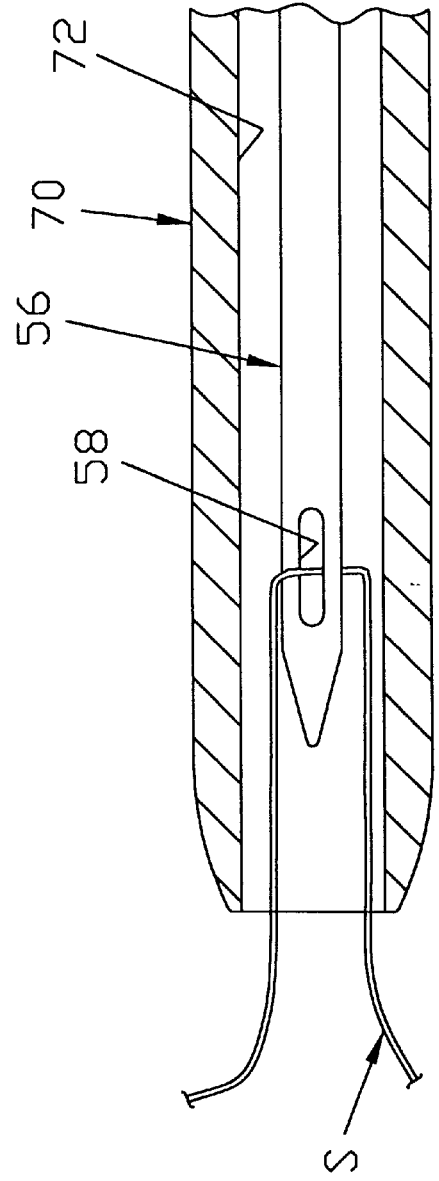
FIG. 28
FIG. 29

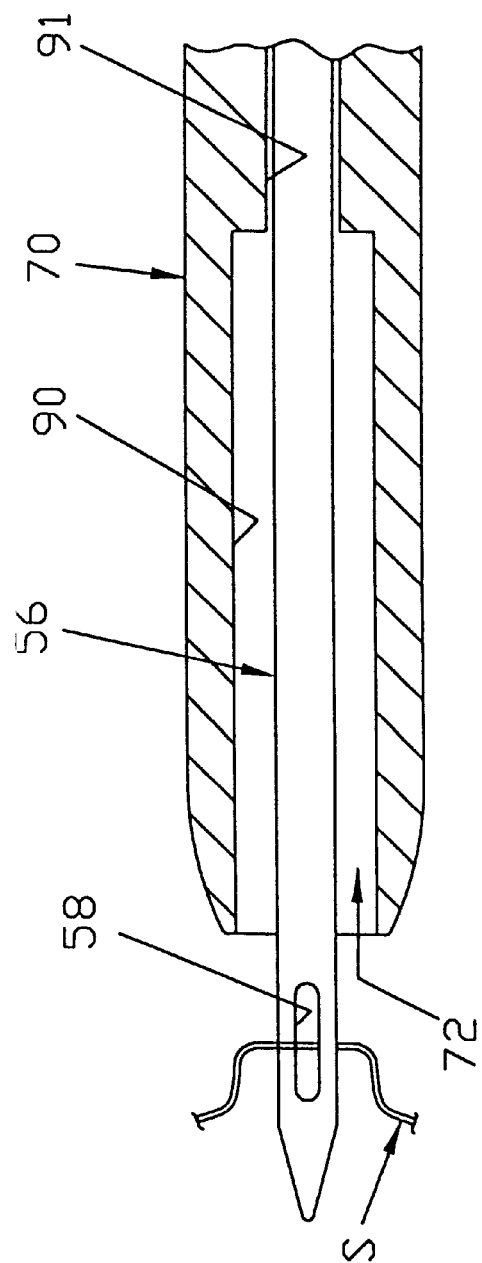
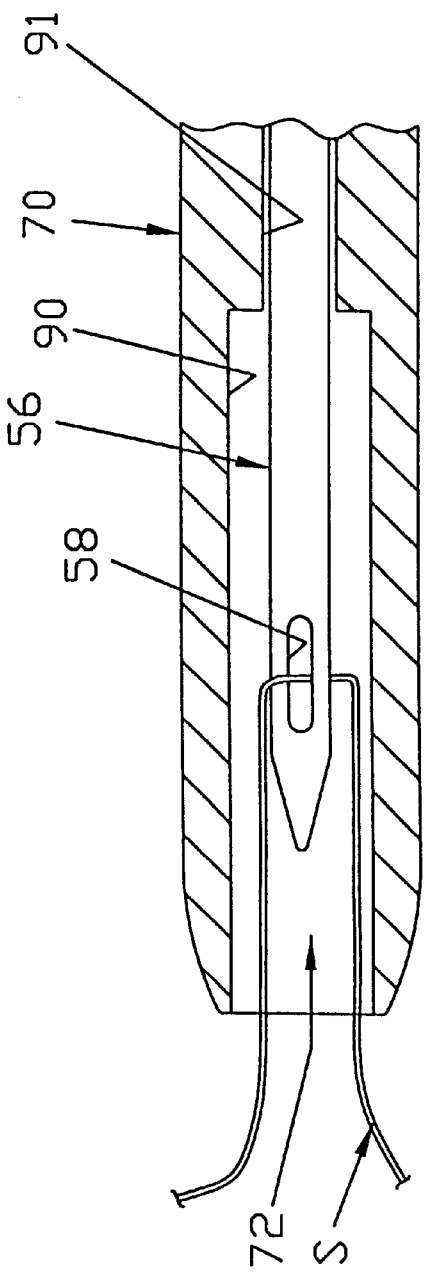

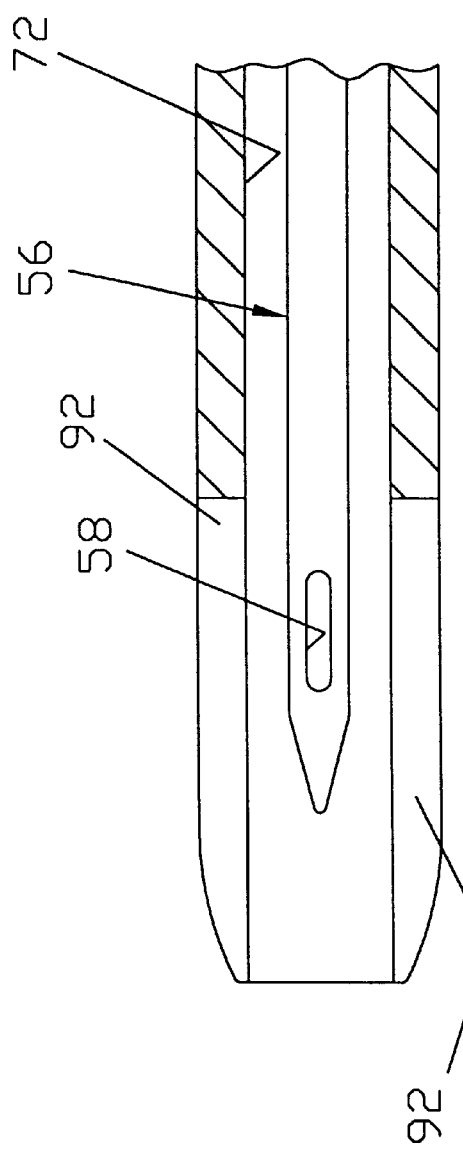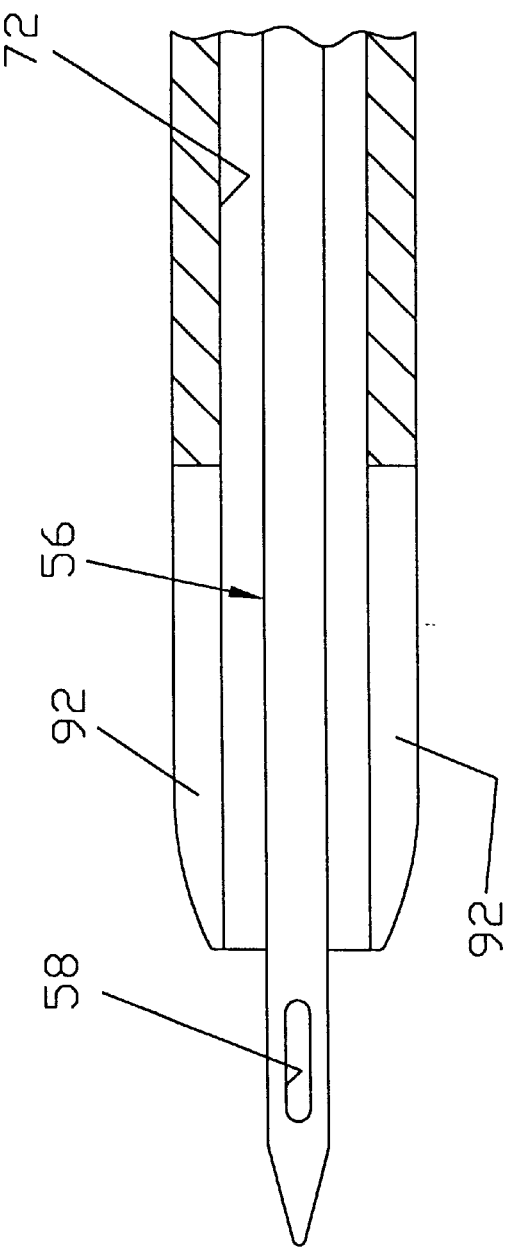

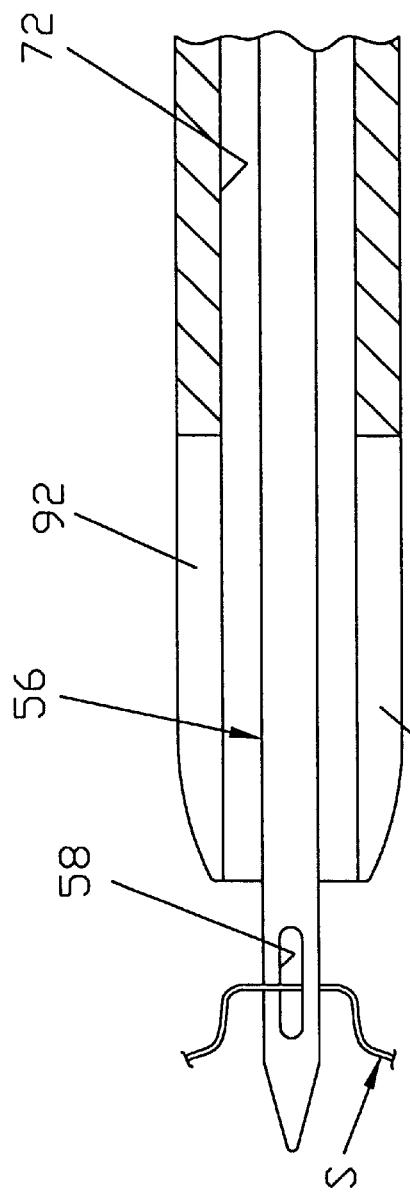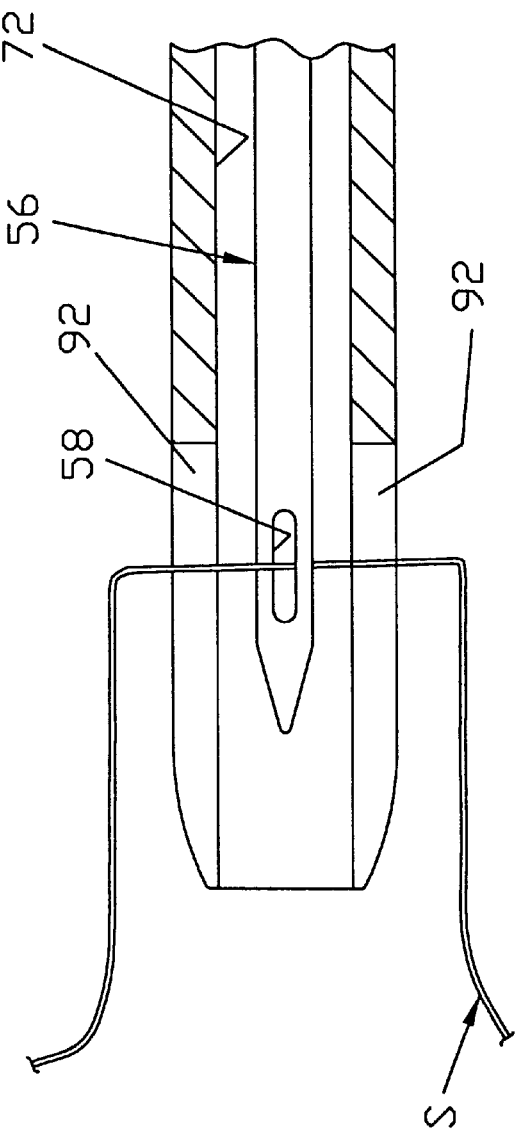

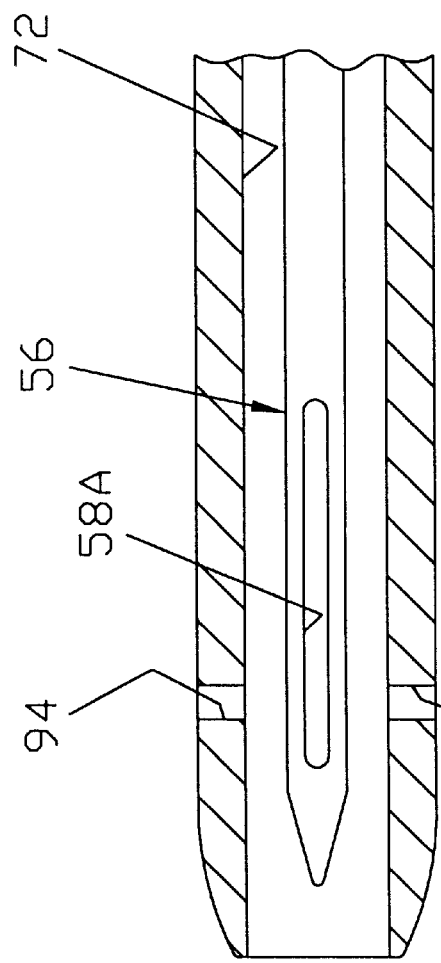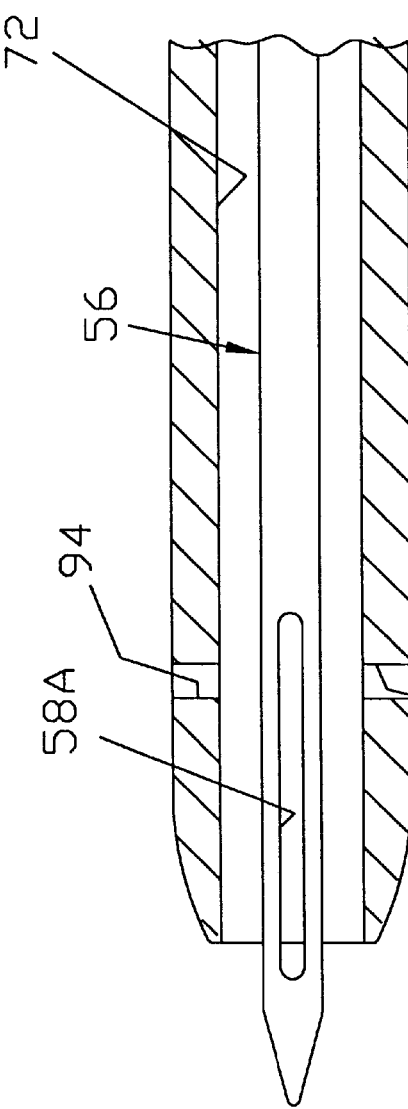

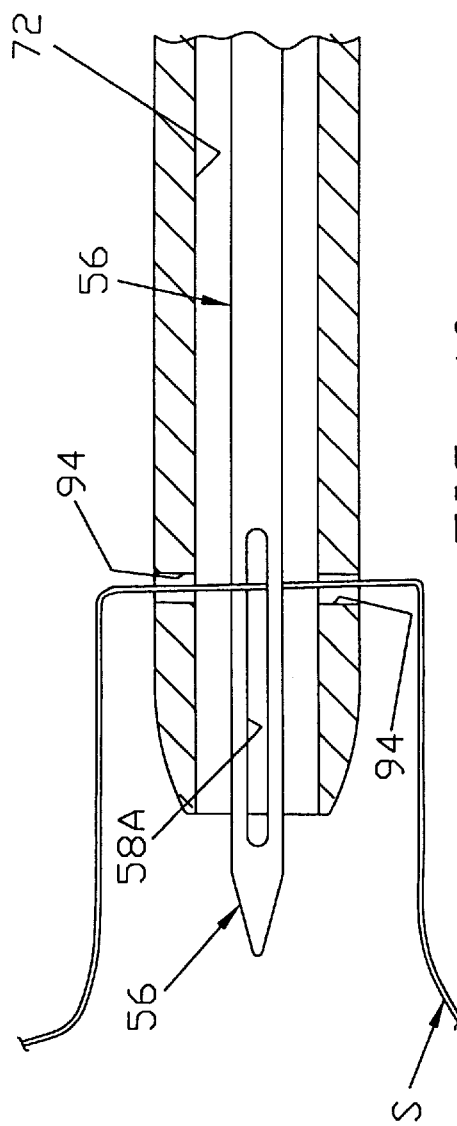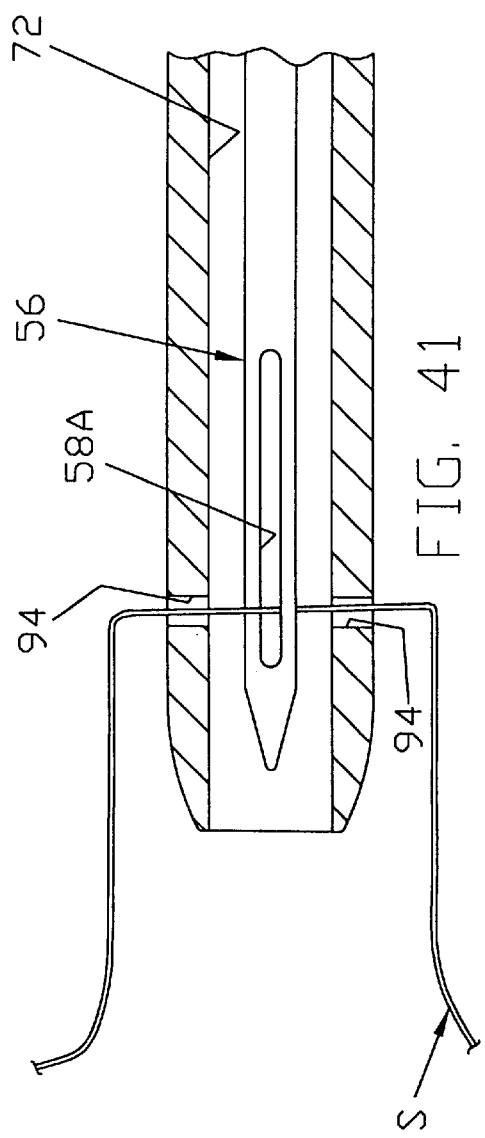

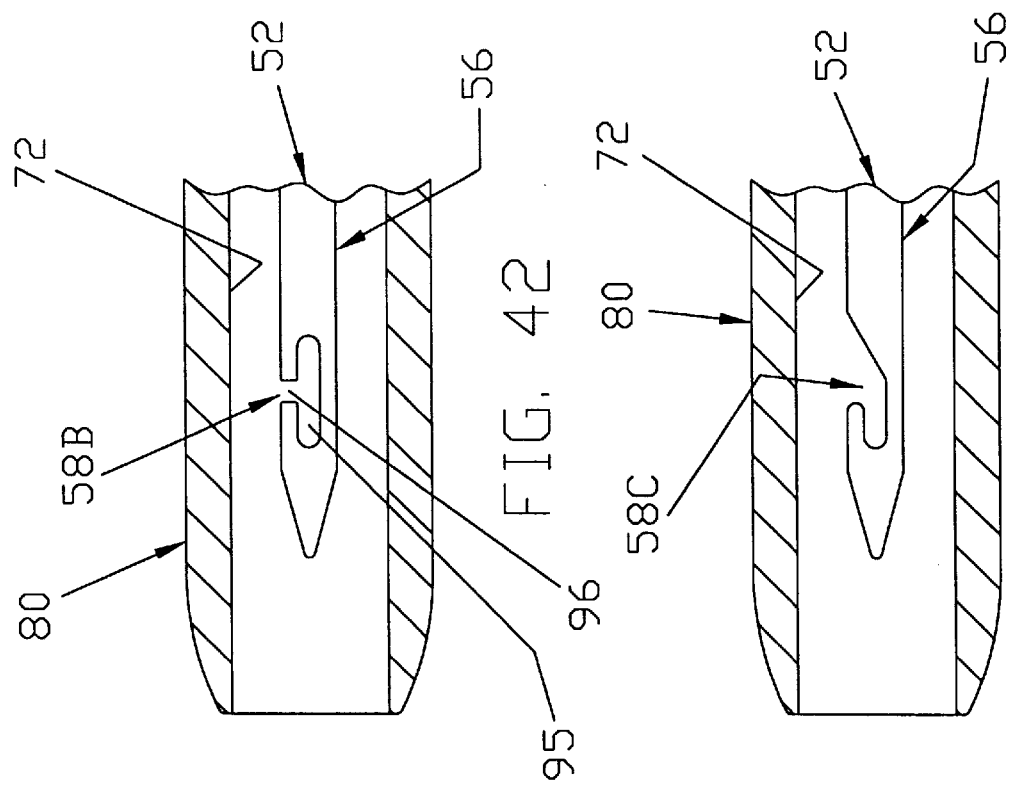

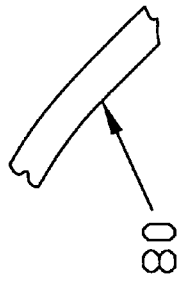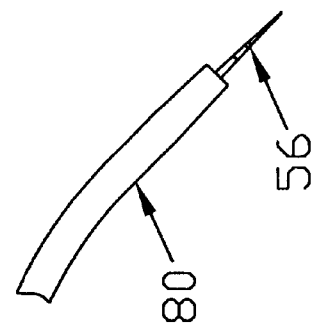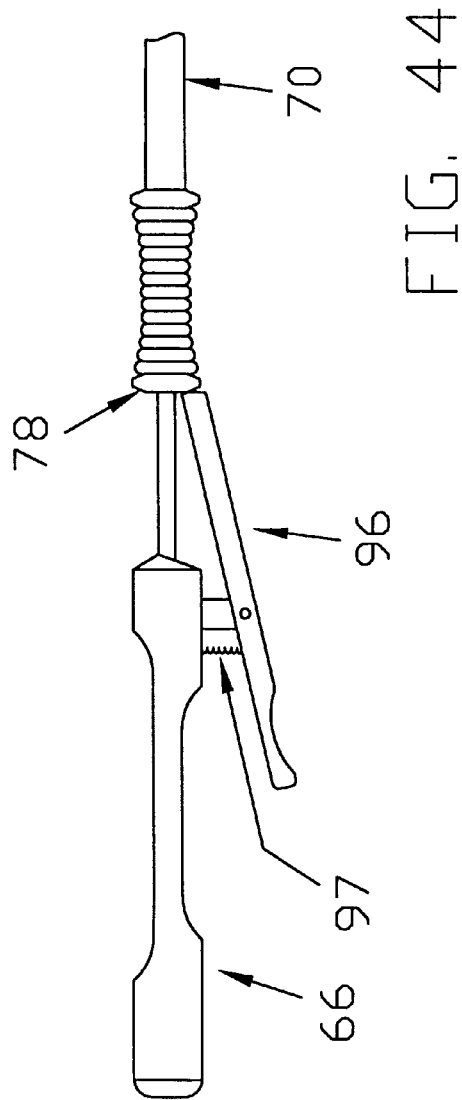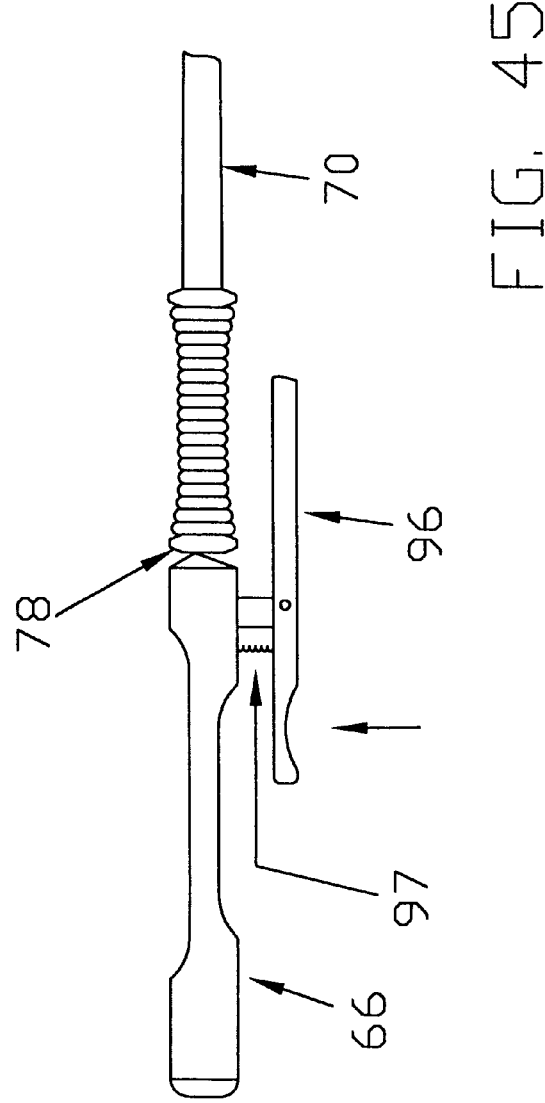
FIG. 44
FIG. 45

NEEDLE ASSEMBLY AND METHOD FOR PASSING SUTURE

FIELD OF THE INVENTION

This invention relates generally to surgical instruments and procedures, and is directed more particularly to a needle assembly and a method for passing suture within the body.

BACKGROUND OF THE INVENTION

Elongated rigid metal needles having pointed distal ends are used in many medical procedures to pass suture through tissue. In some cases the suture is attached to the needle by passing the suture through an eyelet formed in the proximal end of the needle. In other cases the suture is passed through an eyelet formed in the distal end of the needle. The rigid pointed end of the needle is required for penetrating the tissue which is to be sutured, but it is problematic when the needle must be passed safely by adjacent tissue which is not to be sutured.

By way of example, in a so-called "bladder neck suspension" procedure, the sharp needle must initially penetrate surface tissue, move safely past delicate abdominal organs, then puncture the tissues of the vaginal wall, pick up a piece of suture from a cavity below the vaginal wall and carry it back through the vaginal wall, and then safely carry the suture upward through the abdomen, without harming delicate abdominal organs, for connection to a bodily support structure (e.g., the pelvic bone).

Accordingly, there is a need for an improved needle assembly and an improved method for passing suture within the body, wherein the needle assembly provides a needle pointed end for penetration of tissue when desired, and has provision for shielding the needle pointed end when moving the needle pointed end past tissue which is not to be penetrated.

OBJECTS OF THE INVENTION

An object of the invention is therefore to provide an improved needle assembly including a needle distal end which is pointed and exposed for passing through tissue, and is shielded for passing the assembly safely past tissue which is not to be penetrated.

A further object of the invention is to provide an improved method for passing suture within the body, utilizing the improved needle assembly.

SUMMARY OF THE INVENTION

With the above and other objects in view, as will hereinafter appear, a feature of the present invention is the provision of a needle assembly for passing suture within the body. The assembly comprises a rigid needle having a proximal end and a pointed distal end, and an opening in the distal end extending through the needle for retaining a suture therein; a stop element positioned on the needle proximate to, and spaced from, the proximal end of the needle; a sheath having a lengthwise bore therethrough for slidably retaining the needle; and a lock member engageable with the needle stop element to prevent distal movement of the needle in the sheath bore. The needle distal end is movable to an exposed position for passing the assembly through tissue, and is movable to a shielded position within the sheath for passing the assembly safely past tissue which is not to be penetrated.

In accordance with another feature of the invention, there is provided a method for passing suture within the body, the method comprising the steps of: (1) providing a needle assembly comprising an elongated rigid needle having a proximal end and a pointed distal end, and an opening in the distal end extending through the needle for retaining a suture therein; a stop element positioned on the needle proximate to, and spaced from, the proximal end of the needle; a sheath having a lengthwise bore therethrough for slidably retaining the needle; and a lock member engageable with the needle stop element to prevent distal movement of the needle in the sheath bore; (2) positioning the needle proximally in the sheath so as to cause the needle distal end to be located in the sheath distal end, and engaging the lock member with the stop member so as to prevent distal movement of the needle in the sheath; (3) advancing the assembly within the body until the distal end of the sheath is adjacent to a piece of tissue through which a suture is to be passed; (4) disengaging the lock member from the stop element and moving the needle distally until the stop element engages the sheath, so as to cause the needle distal end to extend from the distal end of the sheath; (5) advancing the assembly through the piece of tissue until the needle exits the far side of the piece of tissue; (6) passing a suture through the opening in the needle distal end; (7) drawing the assembly and the suture back through the piece of tissue; and (8) disengaging the suture from the needle.

In accordance with a further feature of the invention, there is provided a method for passing suture within the body, the method comprising the step of providing a needle assembly comprising an elongated rigid needle having a proximal end and a pointed distal end, and an opening in the distal end extending through the needle for retaining a suture therein; a stop element positioned on the needle proximate to, and spaced from, the proximal end of the needle; a sheath having a lengthwise bore therethrough for slidably retaining the needle; and a lock member engageable with the needle stop element to prevent distal movement of the needle in the sheath bore. The method includes the further steps of disengaging the lock member from the stop element and moving the needle distally until the stop element engages a proximal end of the sheath, so as to cause the needle distal end to extend from a distal end of the sheath; advancing the assembly through a first piece of tissue at a first location; and drawing the needle proximally in the sheath so as to cause the needle distal end to re-enter the sheath distal end, and engaging the lock member with the stop element to prevent distal movement of the needle in the sheath. Other steps include advancing the assembly within the body until the distal end of the sheath is adjacent to a second piece of tissue, at a second location, through which suture is to be passed; disengaging the lock member from the stop element and moving the needle distally until the stop element engages the sheath, so as to cause the needle distal end to extend from the distal end of the sheath, and advancing the assembly through the second piece of tissue until the needle exits the far side of the second piece of tissue. A suture is then passed through the opening in the needle distal end, and the assembly and the suture are drawn back through the second piece of tissue, and the suture is disengaged from the needle. The above procedure may be repeated in the second piece of tissue, at a third location, so as to provide two suture free ends extending from the second piece of tissue.

In accordance with a further feature of the present invention, there is provided a needle assembly for passing suture within the body, the assembly comprising a rigid needle having a proximal end and a pointed distal end, and an opening in the distal end extending through the needle for retaining a suture therein; a sheath having a lengthwise bore therethrough for slidably retaining the needle; a lock member engageable with the sheath to prevent distal movement of the needle in the sheath bore; wherein the needle distal end is movable to an exposed position for passing the assembly through tissue, and is movable to a shielded position within the sheath for passing the assembly safely past tissue which is not to be penetrated.

BRIEF DESCRIPTION OF THE DRAWINGS

The above and other objects and features of the present invention will be more fully disclosed or rendered obvious by the following detailed description of the preferred embodiments of the invention, which are to be considered together with the accompanying drawings wherein like numbers refer to like parts, and further wherein:

FIG. 4 is an end elevational view of the needle of FIG. 3;

FIG. 5 is a side elevational view of a sheath portion of the assembly of FIG. 1;

FIG. 6 is a sectional view taken along line 6—6 of FIG. 5;

FIG. 7 is an end elevational view of the sheath of FIG. 5;

FIGS. 11 and 12 are similar to FIG. 1, but show the lock member portion of the sheath, and the needle, in different operating positions;

FIGS. 13–25 and 25A–25C are diagrammatic depictions of a sequence of steps in part showing one method illustrative of an embodiment of the invention;

FIGS. 26–41 are in part centerline sectional, and in part side elevational, views of four alternative embodiments of sheath and needle distal ends, each embodiment being shown in four operating positions;

FIGS. 42 and 43 are in part centerline sectional, and in part side elevational, views of two additional embodiments of needle distal ends; and FIGS. 44 and 45 are side elevational views of yet another form of needle assembly.

DETAILED DESCRIPTION OF THE PREFERRED EMBODIMENTS

Figure 1:
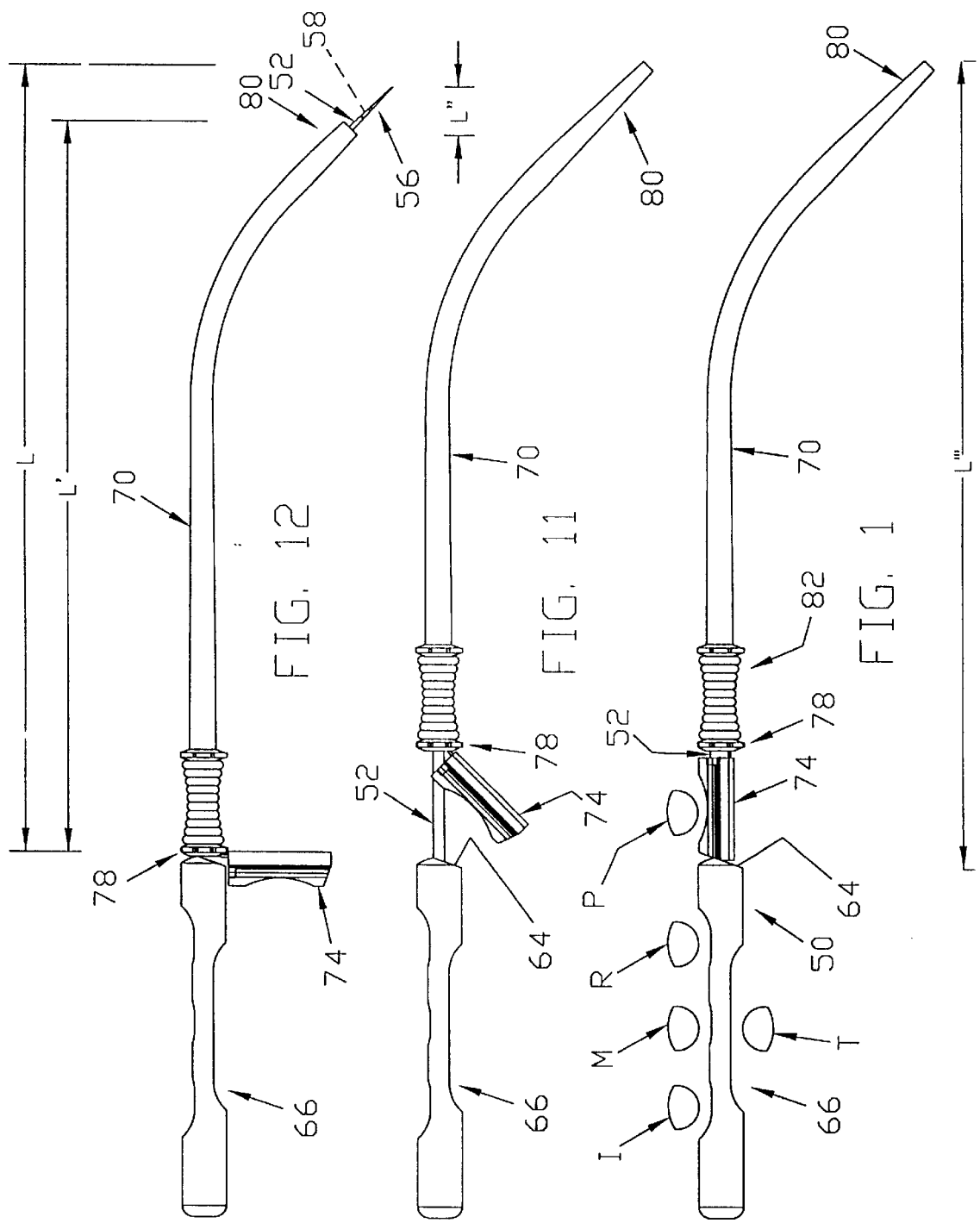
FIG. 1 is a side elevational view of one form of needle assembly illustrative of an embodiment of the invention.
Figure 2:
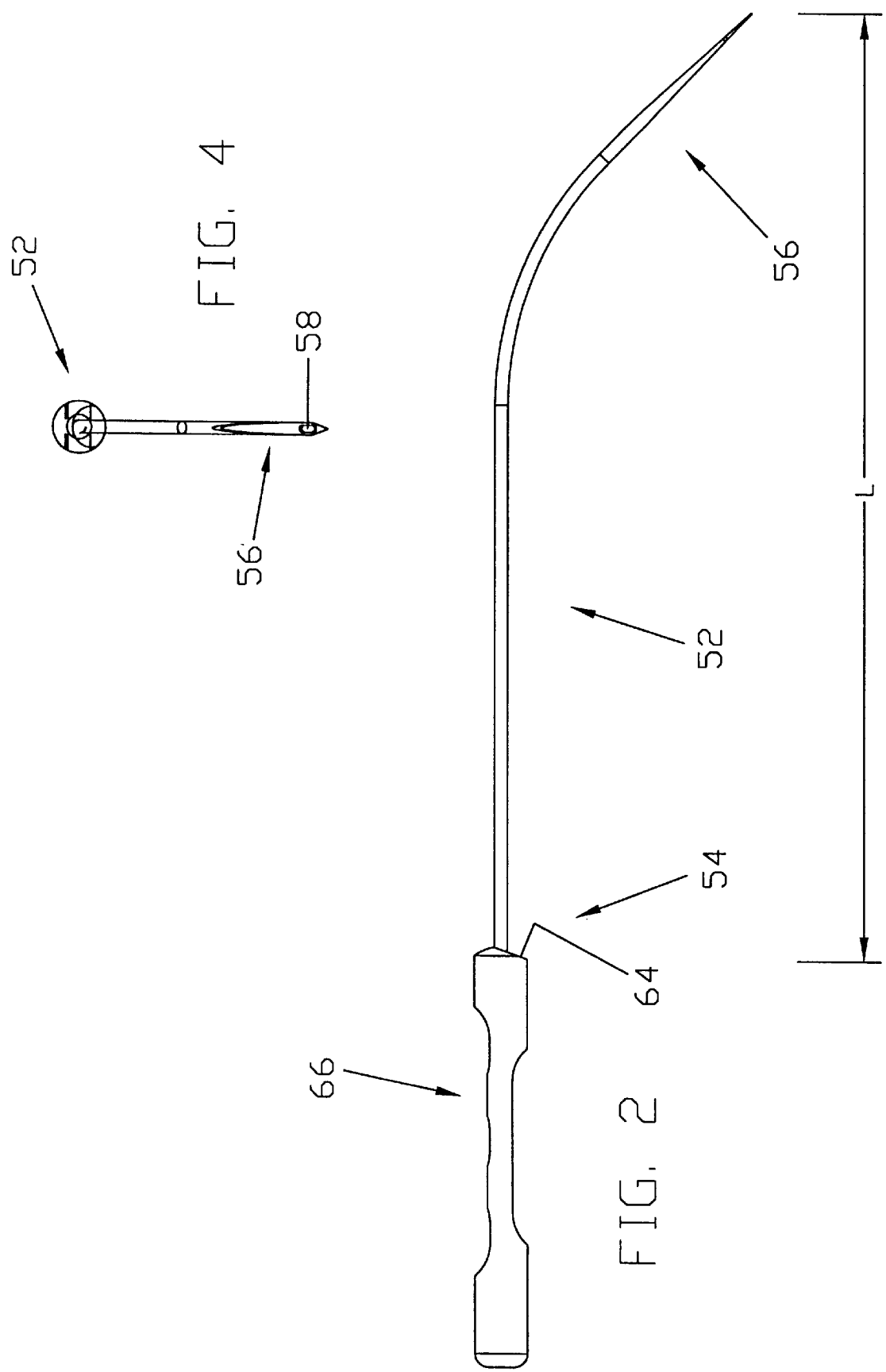
FIG. 2 is a side elevational view of a needle portion of the assembly of FIG. 1.
Figure 3:
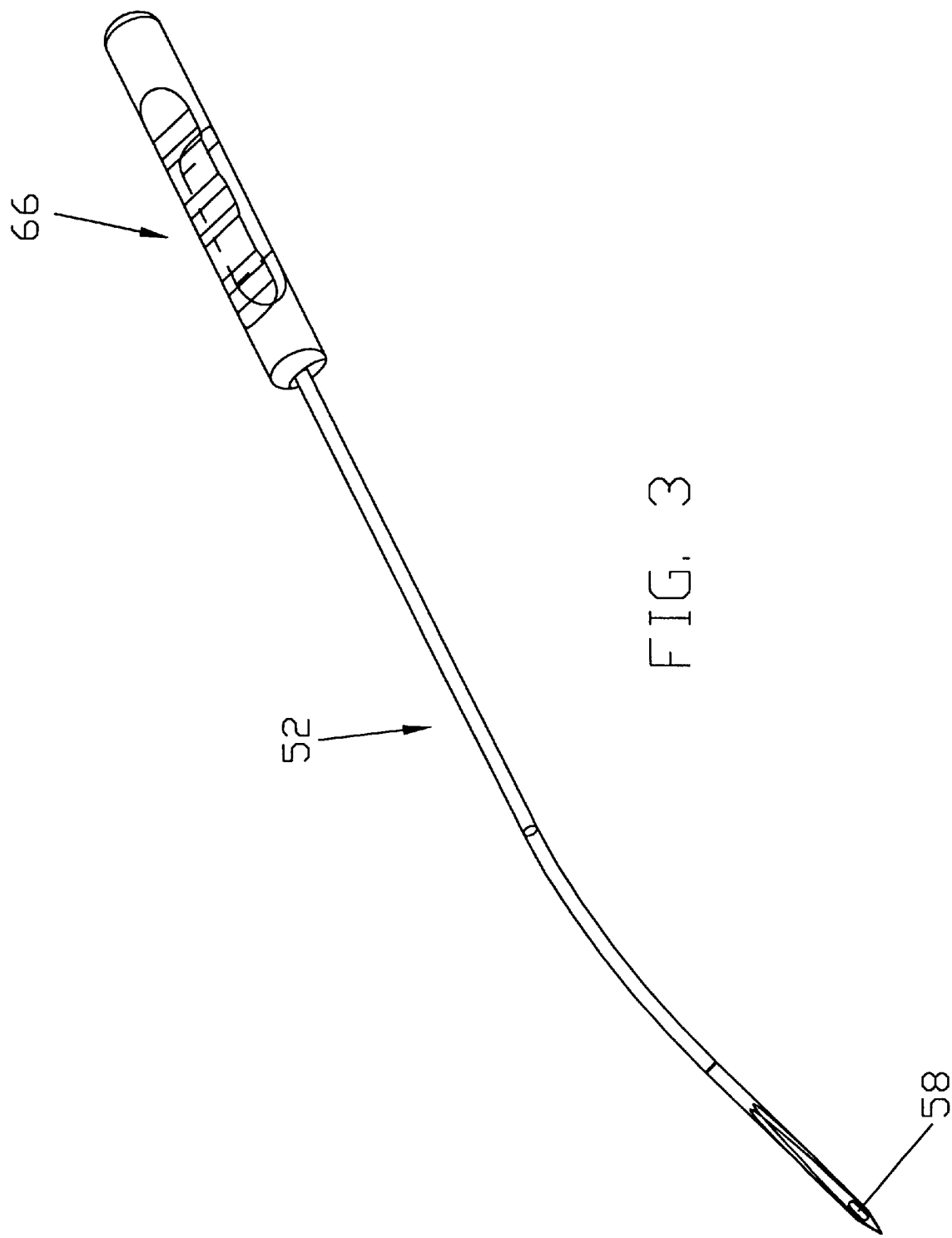
FIG. 3 is a perspective view of the needle of FIG. 2.

Referring first to FIG. 1, it will be seen that an illustrative needle assembly 50 comprises an elongated, rigid needle 52 (FIG. 2) having a proximal end 54 and a distal end 56. An opening, in the form of a round or linear aperture 58 (FIGS. 3, 4, and 26–37) or an elongated slot 58A (FIGS. 38–41) extends through distal end 56 of needle 52, widthwise of the needle, for retaining a suture S (FIGS. 28, 29, 32, 33, 36, 37, 40 and 41) therein. A stop element 64 (FIGS. 1 and 2), preferably in the form of a distal portion of a grip member 66, is positioned on needle 52.

Needle assembly 50 further includes a sheath 70 (FIGS. 1 and 5) having a lengthwise bore 72 (FIG. 6) extending therethrough for slidably receiving needle 52 (FIGS. 11 and 12). Sheath 70 preferably is formed out of a moderately flexible elastomeric or plastic material and is adapted to conform to the shape of rigid needle 52 (FIGS. 1, 11 and 12).

Figure 8:
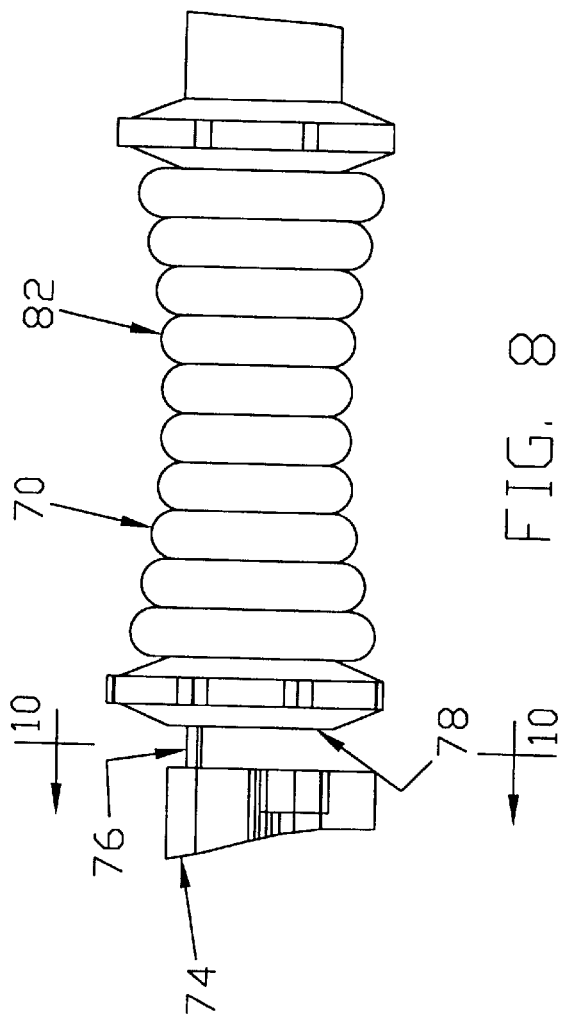
FIG. 8 is an enlarged side elevational view of a portion of the sheath of FIG. 5.
Figure 9:
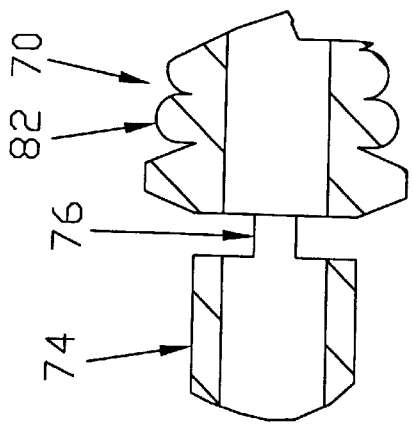
FIG. 9 is an enlarged centerline sectional view of a portion of the sheath of FIG. 6.
Figure 10:
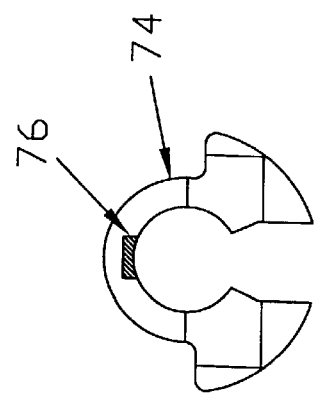
FIG. 10 is a sectional view taken along the line 10—10 of FIG. 8.

A lock member 74 (FIGS. 1, 11 and 12) is engageable by the needle stop element 64 (FIG. 1) in order to prevent distal movement of needle 52 in sheath bore 72. Lock member 74 may be a discrete element removable from sheath 70; or it may be fixed on the sheath, as by a hinge 76; or it may be formed integral with the sheath so as to be fixed thereon, with hinge 76 constituting a living hinge (FIGS. 8–10). Lock member 74 is movable to a position in which the lock member is interposed between needle stop element 64 and a proximal end 78 of sheath 70 (FIG. 1) so as to prevent distal movement of stop element 64, and thereby needle 52. Lock member 74 is further movable (FIG. 11) to another position (FIG. 12) so as to permit stop element 64 (and hence needle 52) to be moved distally toward proximal end 78 of sheath 70. Such movement enables the needle's distal end 56 and opening 58 (or opening 58A) to protrude clear of the distal end 80 of sheath 70 (FIG. 12).

The overall length L (FIG. 12) of needle 52 distally of stop element 64 exceeds the overall length L' (FIG. 12) of sheath 70 by a distance which is at least equal to a length L" (FIG. 12) of needle 52 as measured from distal end 56 thereof to a proximal extent of opening 58. The overall length L (FIG. 2) of needle 52 distally of stop element 64 is less than an overall length L'" (FIG. 1) of sheath 70 and lock member 74 combined. Thus, moving needle stop element 64 against sheath proximal end 78 causes needle distal end 56 and opening 58 to extend clear of sheath distal end 80 (FIG. 12), while holding needle stop element 64 against lock member 74 causes needle distal end 56 and opening 58 to remain within sheath 70 (FIG. 1).

To facilitate handling and operation of the assembly, needle proximal end 54 has fixed thereto the grip member 66 (FIG. 1). Sheath 70 is also provided with a grip portion 82 (FIG. 1) at proximal end 78 of sheath 70. The sheath's grip portion 82 has an outer profile which permits sheath 70 to be conveniently loaded onto needle 52 by gripping the sheath's grip portion 82 between thumb and forefinger and then pulling the sheath proximally back over the needle. The needle's grip member 66 has an outer profile which permits the needle 50 to be conveniently gripped by the user's thumb T (FIG. 1), index finger I, middle finger M, and ring finger R, while the sheath's lock member 74 has an outer profile which permits the lock member to be conveniently pressed away from needle 50 with the user's pinky finger P (see FIGS. 1, 11 and 12).

Sheath 70 is at least in part tapered along a portion of its length such that its distal end 80 is smaller in diameter than its proximal end 78.

The needle's aperture 58 (and slot 58A) is formed so as to allow the suture S to readily pass therethrough, as will be further described hereinbelow.

Figure 26:
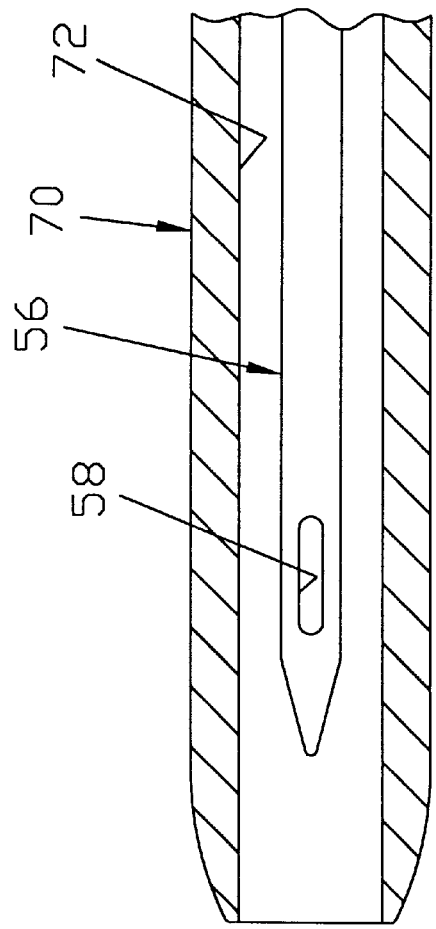

In one exemplary mode of operation, needle assembly 50 is prepared for use by positioning its constituent components in the arrangement shown in FIGS. 1 and 26, wherein the distal end 56 of needle 52 is disposed within sheath 70 and lock member 74 is disposed between needle stop element 64 and proximal end 78 of sheath 70. In other words, needle distal end 56 is safely nested within sheath 70. To prepare for entering through a body surface, lock member 74 is removed (e.g., with the user's pinky finger P) from its interposition between needle stop element 64 and sheath proximal end 78 (FIG. 11). This frees stop element 64, and thereby needle 52, for subsequent distal movement. At this point, needle assembly 50 is in the position shown in FIGS. 11 and 26.

By manipulation of needle grip member 66, an operator brings distal end 80 of sheath 70 to bear against a body surface B (FIG. 13). Using needle grip member 66, the operator then pushes needle 52 distally, causing needle distal end 56 to penetrate body surface B while distal end 80 of sheath 70 remains in engagement with body surface B (FIG. 14). Needle 52 continues to move distally until its stop element 64 engages proximal end 78 of sheath 70, at which point assembly 50 will be in the position shown in FIGS. 12, 15 and 27.

Figure 17:
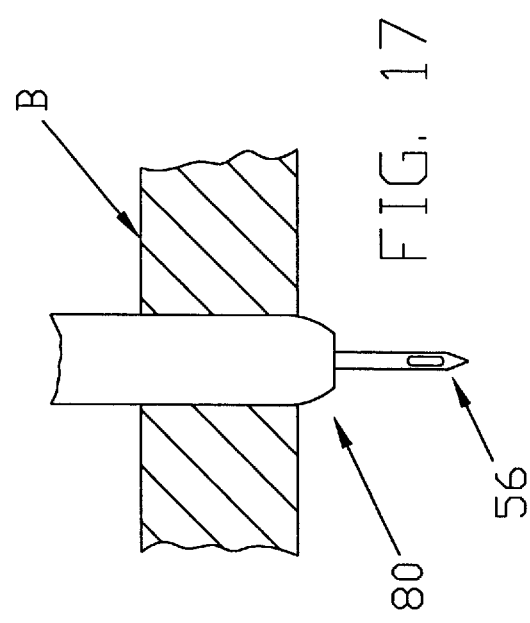
Figure 18:
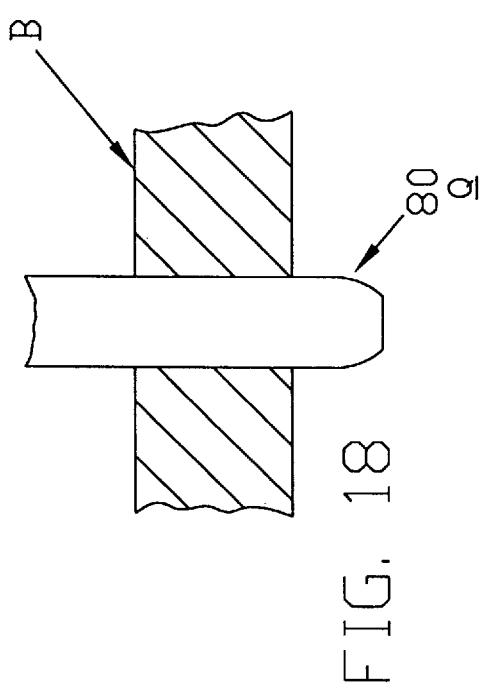
Figure 16:
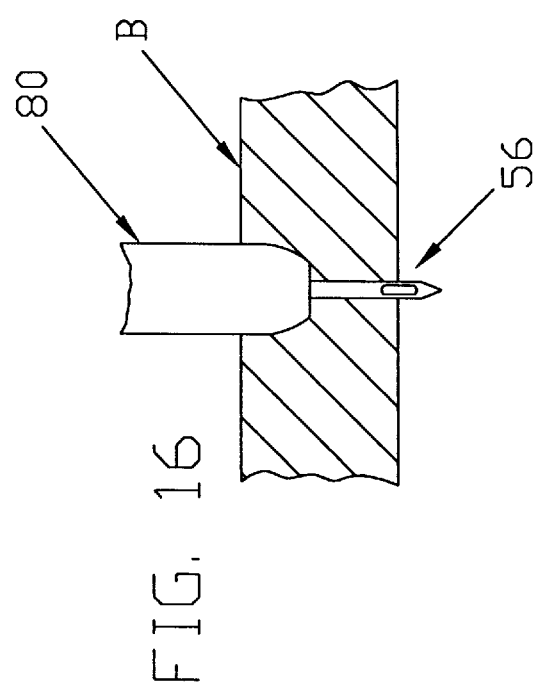

Continued advancement of needle 52 causes sheath 70 as well as needle 52 to move into body surface B (FIGS. 16). Advancement continues until needle 52 and sheath 70 pass completely through body surface B (FIG. 17). The operator then draws needle 52 back into sheath 70 (FIGS. 18 and 26), and then continues advancement of needle assembly 50 through the space Q within the body (FIGS. 18 and 19), towards and into engagement with the tissue V through which suture S is to be passed. In this respect it will be appreciated that, inasmuch as the needle's sharp tip will be safely shielded within sheath 70 as the needle assembly moves through space Q, the risk of the needle's sharp tip inadvertently damaging delicate tissues within space Q will be minimized.

Figure 22:
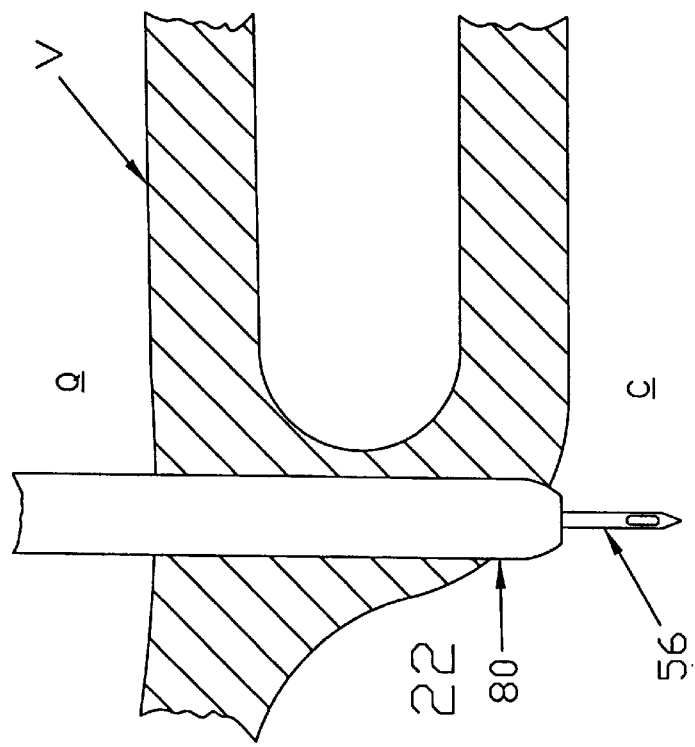
Figure 21:
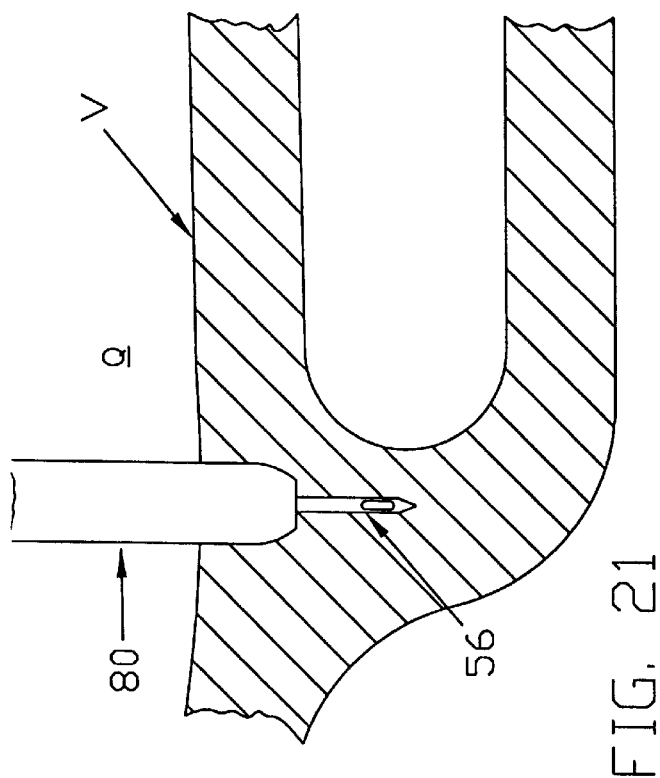
Figure 27:
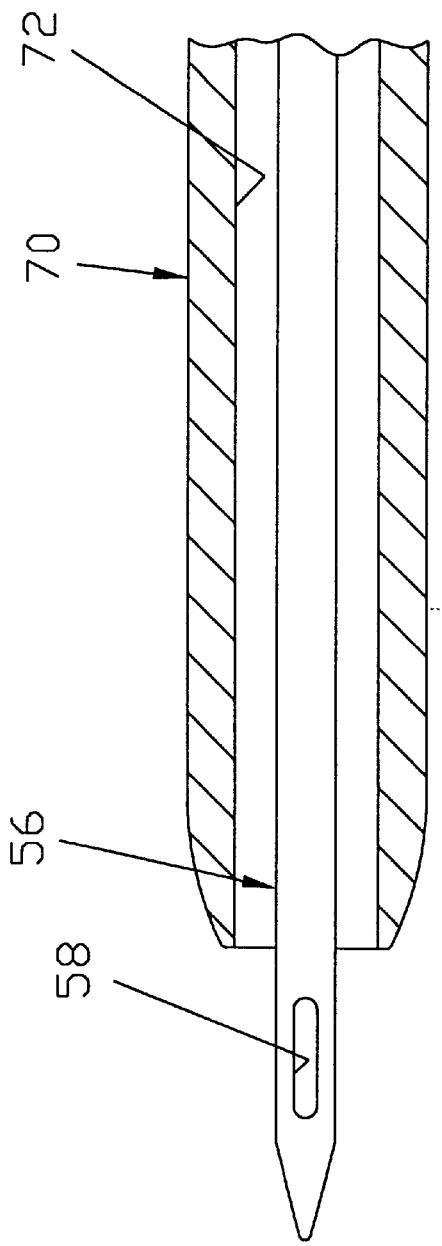

Once the distal end of sheath 70 engages target tissue V (FIG. 19), the operator again manipulates lock member 74 (FIG. 11) so as to free needle 52 for distal movement. The user then advances needle 52 into tissue V, as illustrated in FIGS. 20 and 27. As this occurs, sheath 70 will initially remain engaged with the upper surface of tissue V while needle 52 penetrates into the tissue. Continued advancement of needle 52 will cause needle stop element 64 to engage sheath proximal end 78, whereby sheath 70 will also move into tissue V (FIG. 21). The needle assembly is then further advanced (FIG. 22) until the needle's distal end 56 and opening 58 clear tissue V and reside in a cavity C (FIG. 22) located on the far side of target tissue V. Suture S, introduced into cavity C independently of assembly 50, is then threaded through opening 58 in needle 52 (FIGS. 23 and 28) by means well known in the art. By way of example but not limitation, suture S might be threaded through needle opening 58 using small forceps while under visualization.

With suture S disposed in needle opening 58, needle 52 is withdrawn back into sheath 70 (FIGS. 24 and 29), and then needle assembly 50 is withdrawn from tissue V (FIG. 25) and, ultimately, body surface B. Suture S may be disengaged from needle assembly 50, either before or after the needle assembly is withdrawn through body surface B, leaving suture S extending from cavity C, through tissue V, through body space Q, and then, if desired, through body surface B.

The entire procedure may then be repeated again, at a different location, so as to pass another length of suture through tissue V.

Figure 25A:
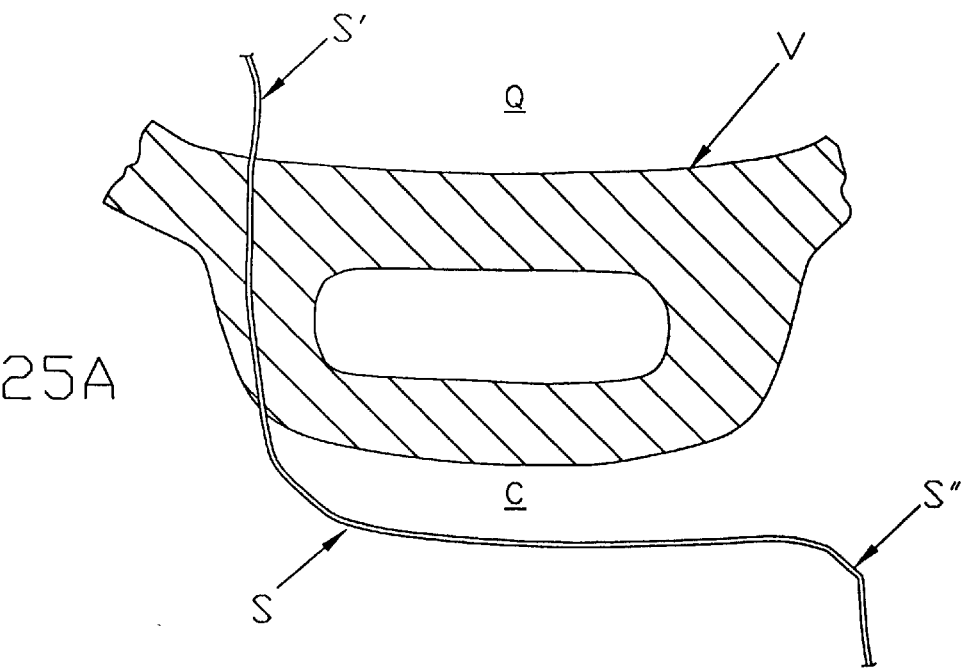
Figure 25B:
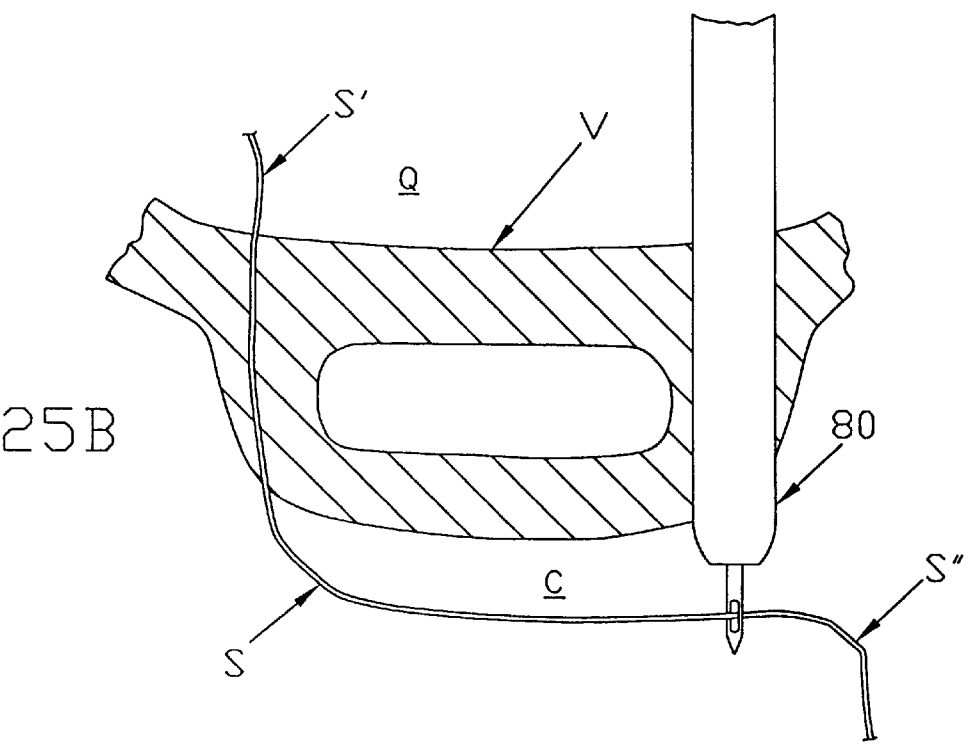
Figure 25C:
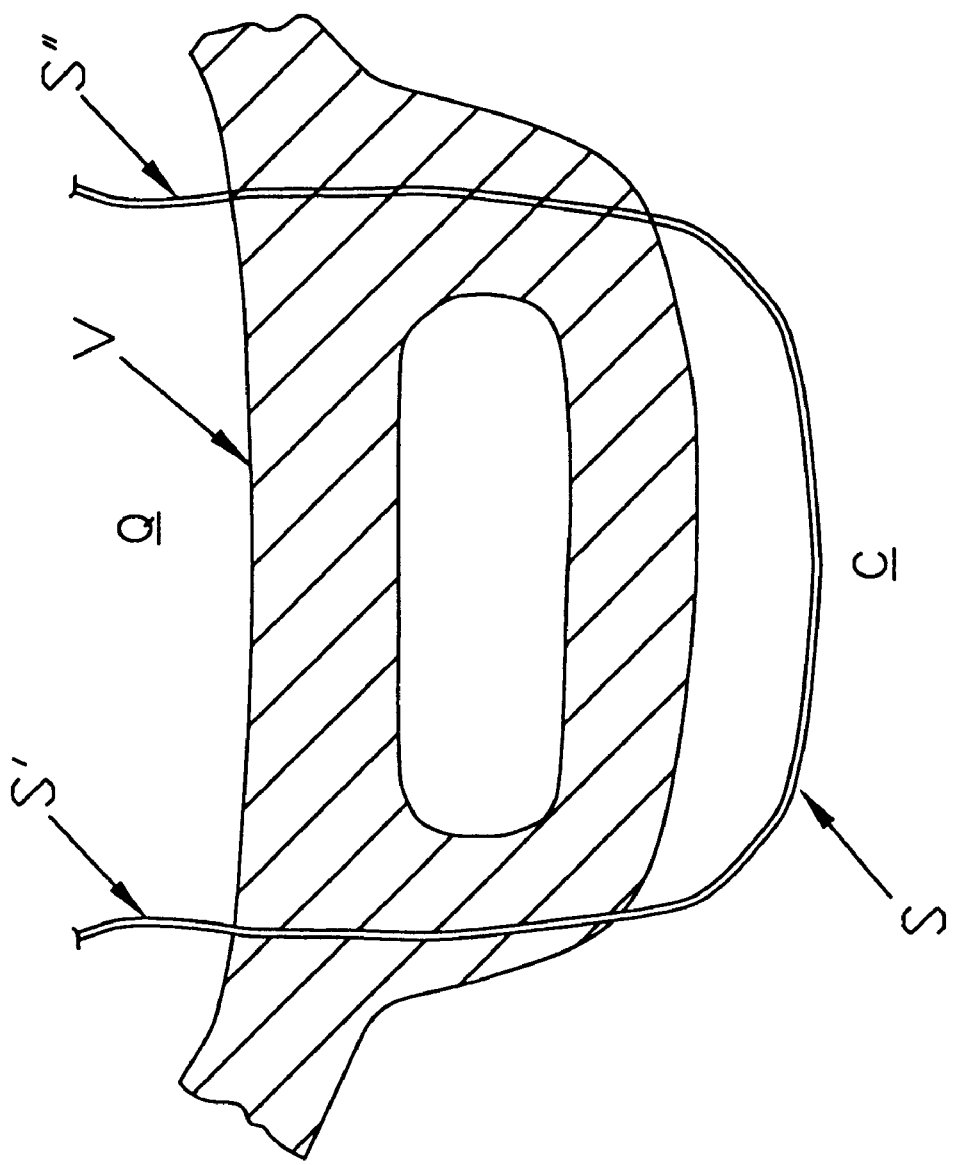

By way of example but not limitation, after the two suture portions S' and S" (FIG. 25) have been passed through tissue V, portion S' can be pulled upward through tissue V, leaving just suture portion S" in the cavity C below tissue V (FIG. 25A). The needle assembly 50 can then be used to penetrate tissue V at another location so as to retrieve tissue portion S" (FIG. 25B) and pull it up through tissue V and across body space Q (FIG. 25C). By properly spacing the tissue penetration points, a loop of the suture S can extend beneath the tissue V such that, by attachment of the free ends of the suture S to a bodily support member (e.g., a bone), the tissue V may be suspended by the suture S.

The above-described procedure is believed to have particular utility in a bladder neck suspension procedure, wherein a needle is passed through the abdominal wall B, through abdominal space Q, through vaginal tissue V and then into the underlying cavity C. Suture is introduced into such cavity and, through known methods, is threaded through an eyelet in the needle. The needle is then withdrawn, drawing a portion of the suture upward therewith, so that it passes through vaginal tissue V. The foregoing procedure is then repeated at another location in the vaginal tissue V, such that pulling on the two free ends of the suture can elevate vaginal tissue V and, thereby, the patient's bladder neck. The above described assembly and method enable the bladder neck suspension procedure to be carried out without risk of injury to the patient's abdominal organs during transit of the needle point from the abdominal wall B to the vaginal tissue V.

More generally, however, the apparatus and method shown and described herein facilitate alternative modes of penetration in the course of any needle penetration activity, namely, a "hard" approach wherein the needle point is exposed for maximum penetration capability, and a "soft" approach for maximum safety in needle advancement.

As noted above, suture S is intended to be drawn into sheath 70 as needle assembly 50 is withdrawn back through tissue V, space Q and, if desired, body surface B. Preferably, but not necessarily, sheath 70 and needle 52 are sized so that suture S can slip relative to needle 52 even when the needle is retracted back into sheath 70 (i.e., when the assembly is in the position shown in FIG. 29).

In FIGS. 30–41, there are shown alternative embodiments of sheath 70, bore 72 and needle openings 58 (and 58A), all permitting slippage of suture S through opening 58 (and 58A) even when needle 52 is in its retracted position within sheath 70.

For example, in FIGS. 30–33, there is shown the bore 72 having an enlarged distal portion 90 which provides ample room around the needle distal end 56 and suture S, as shown in FIG. 33, to permit suture S to readily slip through opening 58, and a relatively confined portion 91 of bore 72 for support of needle 52.

In FIGS. 34–37, there is shown an embodiment in which sheath 70 is provided with axially-extending slots 92 through which suture S extends and can easily slip therethrough, thereby ensuring freedom of suture S to slip through opening 58, shown particularly in FIG. 37.

In FIGS. 38–41, there is shown an embodiment in which sheath 70 is provided with opposed apertures 94 and needle 52 is provided with the elongated slot 58A which can be aligned with the apertures 94 when the needle is extended (FIG. 40) for insertion of suture S, and which remains aligned with apertures 94 when the needle is retracted (FIG. 41), thereby permitting the suture to slip through opening 58A regardless of the position of needle 52 relative to sheath 70.

FIG. 42 illustrates yet another form of needle assembly. In this arrangement, needle 52 is provided with an opening 58B which is in the form of a hole 95 and a side opening 96 which communicates with the hole.

FIG. 43 illustrates still another form of needle assembly. In this construction, needle 52 is provided with an opening 58C which is configured so that the distal end of needle 52 comprises a crochet hook.

FIGS. 44 and 45 illustrate yet another form of needle assembly. In this construction, a lock member 96 is pivotally connected to grip member 66, whereby (i) lock member 96 can engage the proximal end 78 of sheath 70 (FIG. 44) so as to prevent distal movement of the needle within sheath bore 72, and (ii) lock member 96 can be disengaged from the proximal end 78 of sheath 70 (FIG. 45) so as to permit distal movement of the needle within sheath bore 72. A spring 97 may be provided to bias lock member 96 into the position shown in FIG. 44.

There is thus provided an improved needle assembly and method for passing suture within the body and providing to an operator an election between advancing the assembly through body portions in a mode providing maximum tissue penetration capability and a mode providing maximum safety to internal organs and tissue.

It is to be understood that the present invention is by no means limited to the particular construction and method steps herein disclosed and/or shown in the drawings, but also comprises any modifications or equivalents within the scope of the claims.

What is claimed is:

1. A needle assembly for passing suture within the body, said assembly comprising:
    a rigid needle having a proximal end and a pointed distal end, and an opening in said distal end extending through said needle for retaining a suture therein;
    a stop element positioned on said needle proximate to, and spaced from, said proximal end of said needle;
    a sheath having a lengthwise bore therethrough for slidably retaining said needle; and
    a lock member engageable with said stop element to prevent distal movement of said needle in said sheath bore, said lock member being hingedly attached to said sheath;
    wherein said needle distal end is movable to an exposed position for passing said assembly through tissue, and is movable to a shielded position within said sheath for passing said assembly safely past tissue which is not to be penetrated.

2. An assembly according to claim 1 wherein said lock member is attached to said sheath by a living hinge.

3. An assembly according to claim 1 wherein said stop element comprises a block fixed on said needle, and said lock member is engageable with said block to prevent movement thereof, and thereby said needle, distally in said sheath.

4. An assembly according to claim 1 wherein said lock member is hingedly movable to a first position between said stop element and a proximal end of said sheath so as to prevent distal movement of said needle in said sheath, and is hingedly movable to a second position removed from said first position so as to permit said needle to move distally in said sheath.

5. An assembly according to claim 1 wherein said needle proximal end has fixed thereon a grip member.

6. An assembly according to claim 5 wherein said sheath has disposed thereon a grip portion.

7. An assembly according to claim 1 wherein at least a portion of said sheath is tapered such that said distal end thereof is smaller in diameter than said proximal end thereof.

8. An assembly according to claim 1 wherein said opening comprises an aperture.

9. An assembly according to claim 1 wherein an overall length of said needle distally of said stop element exceeds an overall length of said sheath by a distance at least equal to the length of said needle from said distal end thereof to a proximal extent of said opening, and wherein said overall length of said needle distally of said stop element is less than an overall length of said sheath and said lock member combined.

10. An assembly according to claim 1 wherein said needle opening is larger in width than a cross-section of the suture, and said bore proximate said distal end of said sheath is sufficiently spaced from said needle when said needle distal end is disposed in said bore, such that the suture is movable through said opening and said sheath distal end as said assembly is withdrawn from a site of attachment of the suture to said needle.

11. An assembly according to claim 10 wherein a portion of said bore proximal of said bore proximate said distal end of said sheath is sized to support said needle in said bore.

12. An assembly according to claim 1 wherein said opening extends widthwise through said needle.

13. An assembly according to claim 1 wherein said opening comprises a round hole.

14. An assembly according to claim 1 wherein said opening comprises an elongated hole, and a side opening extending through said needle so as to communicate with said elongated hole.

15. An assembly according to claim 1 wherein said opening is configured so that said distal end of said needle comprises a crochet hook.

16. A needle assembly for passing suture within the body, said assembly comprising:
    a rigid needle having a proximal end and a pointed distal end, and an open in said distal end extending through said needle for retaining a suture therein;
    a stop element positioned on said needle proximate to, and spaced from, said proximal end of said needle;
    a sheath having a lengthwise bore therethrough for slidably retaining said needle; and
    a lock member engageable with said stop element to prevent distal movement of said needle in said sheath bore;
    wherein said needle opening is larger in width than a cross-section of the suture, and said sheath is provided with slots extending proximally from a distal end of said sheath, said slots having widths exceeding the width of the suture, such that the suture is movable through said opening and said sheath slots as said assembly is withdrawn from a site of attachment of the suture to said needle, and
    wherein said needle distal end is movable to an exposed position for passing said assembly through tissue, and is movable to a shielded position within said sheath for passing said assembly safely past tissue which is not to be penetrated.

17. A needle assembly for passing suture within the body, said assembly comprising:
    a rigid needle having a proximal end and a pointed distal end, and an opening in said distal end extending through said needle for retaining a suture therein;
    a stop element positioned on said needle proximate to, and spaced from, said proximal end of said needle;
    a sheath having a lengthwise bore therethrough for slidably retaining said needle; and
    a lock member engageable with said stop element to prevent distal movement of said needle in said sheath bore;
    wherein said needle opening comprises an elongated slot larger in width than a cross-section of the suture, and said sheath is provided with opposed, radially-extending apertures, a first portion of said elongated slot being alignable with said apertures when said needle is extended beyond said sheath, and a second portion of said elongated slot being alignable with said apertures when said needle is retracted into said sheath, said apertures having a diameter larger than the diameter of the suture, such that the suture is movable through said opening and said sheath apertures as said assembly is withdrawn from a site of attachment of the suture to said needle, and wherein said needle distal end is movable to an exposed position for passing said assembly through tissue, and is movable to a shielded position within said sheath for passing said assembly safely past tissue which is not to be penetrated.

18. A method for passing suture within the body, the method comprising the steps of:
(1) providing a needle assembly comprising:
   (a) a rigid needle having a proximal end and a pointed distal end, and an opening in said distal end extending through said needle for retaining a suture therein;
   (b) a stop element positioned on said needle proximate to, and spaced from, said proximal end of said needle;
   (c) a sheath having a lengthwise bore therethrough for slidably retaining said needle; and
   (d) a lock member engageable with said stop element to prevent distal movement of said needle in said sheath bore, said lock member being hingedly attached to said sheath;
(2) positioning said needle proximally in said sheath so as to cause said needle distal end to be located in said sheath distal end, and engaging said lock member with said stop member so as to prevent distal movement of said needle in said sheath;
(3) advancing said assembly within said body until said distal end of said sheath is adjacent to a piece of tissue through which a suture is to be passed;
(4) disengaging said lock member from said stop element and moving said needle distally until said stop element engages said sheath, so as to cause said needle distal end to extend from said distal end of said sheath;
(5) advancing said assembly through said piece of tissue until said needle exits the far side of said piece of tissue;
(6) passing a suture through said opening in said needle distal end;
(7) drawing said assembly and said suture back through said piece of tissue; and
(8) disengaging said suture from said needle.

19. A method for passing suture within the body, the method comprising the steps of:
(1) providing a needle assembly comprising:
   (a) a rigid needle having a proximal end and a pointed distal end, and an opening in said distal end extending through said needle for retaining a suture therein;
   (b) a stop element positioned on said needle proximate to, and spaced from, said proximal end of said needle;
   (c) a sheath having a lengthwise bore therethrough for slidably retaining said needle; and
   (d) a lock member hingedly attached to said sheath and engageable with said stop element to prevent distal movement of said needle in said sheath bore;
(2) disengaging said lock member from said stop element and moving said needle distally until said stop element engages said sheath, so as to cause said needle distal end to extend from a distal end of said sheath;
(3) advancing said assembly through a first piece of tissue at a first location;
(4) drawing said needle proximally in said sheath so as to cause said needle distal end to re-enter said sheath distal end, and engaging said lock member with said stop member to prevent distal movement of said needle in said sheath;
(5) advancing said assembly within said body until said distal end of said sheath is adjacent to a second piece of tissue, at a second location, through which a suture is to be passed;
(6) disengaging said lock member from said stop element and moving said needle distally until said stop element engages said sheath, so as to cause said needle distal end to extend from said distal end of said sheath;
(9) advancing said assembly through said second piece of tissue until said needle exits the far side of said second piece of tissue;
(10) passing a suture through said opening in said needle distal end;
(11) drawing said assembly and said suture back through said second piece of tissue; and
(12) disengaging said suture from said needle.

20. A method according to claim 19 wherein steps (4)–(11) are repeated in said second piece of tissue, at a third location, so as to provide two suture free ends extending from said second piece of tissue.

21. A method according to claim 19 wherein said opening comprises an aperture.

22. A method according to claim 19 wherein said stop element comprises a body fixed to said needle.

23. A method according to claim 19 wherein said sheath is tapered such that a distal end of said sheath is of a smaller diameter than a proximal end of said sheath.

24. A method according to claim 19 wherein said stop element is engageable with a proximal end of said sheath when said lock member is not engagement with said stop element.

25. A method according to claim 19 wherein said first piece of tissue comprises abdominal wall, and said second piece of tissue comprises vaginal tissue.

26. A method according to claim 19 including the additional step of fixing said suture to a bodily support member.

27. A method according to claim 19 wherein an overall length of said needle distally of said stop element exceeds an overall length of said sheath by a distance at least equal to the length of said needle from said distal end thereof to a proximal extent of said opening, and wherein said overall length of said needle distally of said stop element is less than an overall length of said sheath and said lock member combined.

28. A needle assembly for passing suture within the body, said assembly comprising:
a rigid needle having a proximal end and a pointed distal end, and an opening in said distal end extending through said needle for retaining a suture therein;
a sheath having a lengthwise bore therethrough for slidably retaining said needle;
a lock member pivotally attached to said needle and engageable with said sheath to prevent distal movement of said needle in said sheath bore;
wherein said needle distal end is movable to an exposed position for passing said assembly through tissue, and is movable to a shielded position within said sheath for passing said assembly safely past tissue which is not to be penetrated.

29. A needle assembly for passing suture within the body, said assembly comprising:

a needle having an axial length, a proximal end, pointed distal end, and an opening in said distal end extending through said needle for retaining a suture therein;

a stop element positioned on said needle proximate to, and spaced from, said proximal end of said needle;

a sheath including a distal end and a proximal end, having a shorter axial length than said axial length of said needle, and having a lengthwise bore therethrough for slidably receiving a portion of said needle such that said pointed distal end of said needle may be moved relative to said sheath between a first position wherein said pointed distal end resides within said distal end of said sheath and a second position wherein said pointed distal end of said needle projects outwardly from said distal end of said sheath; and a lock member pivotally attached to said assembly for releasable engagement between said stop element and said proximal end of said sheath when said needle is in said first position;

whereby said needle distal end is movable relative to said sheath into said second position for the passing of said assembly through tissue, and is movable relative to said sheath into, and lockable in, said first position at other times.

* * * * *